(12) United States Patent
Behling

(10) Patent No.: US 7,949,102 B2
(45) Date of Patent: May 24, 2011

(54) MULTIPLE FOCAL SPOT X-RAY TUBE WITH MULTIPLE ELECTRON BEAM MANIPULATING UNITS

(75) Inventor: Rolf Karl Otto Behling, Norderstedt (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 12/513,861

(22) PCT Filed: Oct. 30, 2007

(86) PCT No.: PCT/IB2007/054397
§ 371 (c)(1),
(2), (4) Date: May 7, 2009

(87) PCT Pub. No.: WO2008/056299
PCT Pub. Date: May 15, 2008

(65) Prior Publication Data
US 2010/0046712 A1 Feb. 25, 2010

(30) Foreign Application Priority Data
Nov. 10, 2006 (EP) .................................... 06123817

(51) Int. Cl.
*H01J 35/08* (2006.01)
(52) U.S. Cl. ........................................ 378/124; 378/119
(58) Field of Classification Search .................. 378/124, 378/167, 168, 205–206, 207, 119
See application file for complete search history.

(56) References Cited

U.S. PATENT DOCUMENTS

| | | | |
|---|---|---|---|
| 6,252,935 B1 | 6/2001 | Styrnol et al. | |
| 6,282,263 B1 | 8/2001 | Arndt et al. | |
| 6,778,633 B1 | 8/2004 | Loxley et al. | |
| 6,895,079 B2 | 5/2005 | Birdwell et al. | |
| 7,001,071 B2 | 2/2006 | Deuringer et al. | |
| 7,317,785 B1* | 1/2008 | Zou et al. ...................... | 378/137 |
| 2005/0029957 A1 | 2/2005 | Lemaitre et al. | |
| 2005/0053189 A1 | 3/2005 | Gohno et al. | |
| 2005/0063514 A1* | 3/2005 | Price et al. .................... | 378/119 |
| 2006/0002515 A1 | 1/2006 | Huber et al. | |

FOREIGN PATENT DOCUMENTS
FR 2555359 A1 5/1985
* cited by examiner

Primary Examiner — Hoon Song

(57) ABSTRACT

A multiple focal spot X-ray tube (100) comprising an electron source (105), which is adapted to generate an electron beam (106), an anode (110), which is arranged within the electron beam (106) and which comprises a first focal spot portion (120) and a second focal spot portion (130), whereby the second focal spot portion (130) is spatially separated from the first focal spot portion (120). The X-ray tube (100) further comprises a first electron beam manipulation unit (125), which is adapted to interact with the electron beam (106), when the electron beam (106) impinges onto the first focal spot portion (120), and a second electron beam manipulation unit (135), which is adapted to interact with the electron beam (106), when the electron beam (106) impinges onto the second focal spot portion (130). By assigning one electron beam manipulation unit (125, 135) to each of the focal spot portions (120, 130), a precise focusing of the X-ray beam can be realized individually for each focal spot of the X-ray tube (100). Preferably, the first and the second focal spot portions have a distance along the axis of a rotating anode.

20 Claims, 5 Drawing Sheets

MULTIPLE FOCAL SPOT X-RAY TUBE WITH MULTIPLE ELECTRON BEAM MANIPULATING UNITS

FIELD OF INVENTION

The present invention relates to the field of generating X-rays by means of X-ray tubes. In particular, the present invention relates to an X-ray tube, which is adapted to generate an X-ray beam being capable of originating sequentially and periodically from at least two different focal spot positions. Such types of X-ray tubes are called multiple focal spot X-ray tubes.

The present invention further relates to an X-ray system, in particular to a medical X-ray imaging system, wherein the X-ray system comprises an X-ray tube as mentioned above.

Further, the present invention relates to a method for generating X-rays, which are in particular used for medical X-ray imaging. The X-rays are generated by means of an X-ray tube as mentioned above.

ART BACKGROUND

Computed tomography (CT) is a standard imaging technique for radiology diagnosis. However, the use of an X-ray tube comprising only a single focal spot sometimes causes reconstruction problems in particular when large objects have to be examined. Thereby, for a certain viewing angle border regions of the object may not be located within the X-ray beam originating from the single focal spot and impinging onto the detector. This has the effect that for these border regions only a reduced number of projection views are available such that the quality of the three-dimensional (3D) reconstruction of the object under examination is reduced. In particular reconstruction artifacts may be generated, which erroneously indicate structures, which are in reality not existent.

In order to increase the available number of projection views also for border regions, dual focal spot X-ray tubes can be used. Thereby, for each viewing angle of a CT scanning unit comprising the X-ray source and the X-ray detector two two-dimensional (2D) X-ray attenuation datasets representing two different projection angles can be generated. Of course, the spatial distance between the two focal spots defines the angular difference between these two 2D X-ray attenuation datasets.

US 2005/0063514 A1 discloses an extended multi-spot CT X-ray source. The described X-ray source comprises an electron gun capable of producing a plurality of electron beams, each electron beam being focused at a predetermined distance and aimed in a predetermined direction. The described X-ray source further comprises and a plurality of targets positioned to receive the electron beams and generate X-rays in response thereto, whereby each target comprises a predetermined focal spot thereon. Each electron beam is synchronized to strike, at an appropriate time, a predetermined target comprising a predetermined focal spot thereon.

US 2005/0053189 A1 discloses an X-ray CT apparatus capable of imaging a subject based on X-rays of multiple energy levels. The CT apparatus comprises an X-ray tube, which generates X-rays from multiple focal points of different 3D positions sequentially on a time-division basis. A plurality of filters are provided, which implement the filtering individually for the X-rays generated individually from the focal points. The anode of the X-ray tube has multiple impingement portions where electrons released by a cathode of the X-ray tube impinge at multiple positions on the trajectory of electrons sequentially on a time-division basis.

U.S. Pat. No. 6,282,263 B1 discloses an X-ray generator comprising an evacuated and sealed X-ray tube, an electron gun, an X-ray target, an internal electron mask, and an X-ray window consisting of a thin tube of material with low X-ray absorption and high mechanical strength. The generator preferably includes a system for focusing and steering the electron beam onto the X-ray target, a cooling system to cool the target material, kinematic mounts to allow precise and repeatable mounting of X-ray devices for focusing the X-ray beam, and X-ray focusing devices of varying configurations and methods.

U.S. Pat. No. 6,778,633 B1 discloses an X-ray generator comprising an evacuated and sealed X-ray tube. The X-ray tube contains an electron gun and an X-ray target. An electron beam is produced by the electron gun consisting of a filament just inside the aperture of a Wehnelt grid. The Wehnelt grid is biased negatively with respect to the filament. Two sets of beam deflection coils are, employed in two planes, mounted between the anode of the electron gun and a focusing lens to center the beam. Between the focusing lens and the target is an air-cored quadrupole magnet, which acts as a stigmator in that it turns the circular cross-section of the beam into an elongated one.

U.S. Pat. No. 6,895,079 B2 discloses a multiple focal spot X-ray inspection system comprising an X-ray source having means for generating more than one beam defining an inspection plane, the beams being substantially parallel to each other. The X-ray inspection system further comprises an X-ray detector having a plurality of detector arrays, each of which is aligned with one of the beams. The means for generating more than one beam may include an electron gun and means for steering an electron beam generated by the gun to multiple focal spots on a target.

U.S. Pat. No. 6,252,935 B1 discloses an X-ray radiator having an x-ray tube with a deflection arrangement that deflects the electron beam of the x-ray tube dependent on a control signal such that the position of the focal spot on the anode corresponds to a reference position changing as a function of time. A detector acquires the actual position of the focal spot and a control unit is supplied with the actual value signal and a reference signal and generates the control signal. The described X-ray radiator has the disadvantage that a precise focusing of the electron beam gets rather difficult in particular when the spatial distance between various focal spot positions is comparatively large.

There may be a need for providing a multiple focal X-ray tube, which allows for an easy and reliable focusing of the different electron beams being assigned to different focal spot positions.

SUMMARY OF THE INVENTION

This need may be met by the subject matter according to the independent claims. Advantageous embodiments of the present invention are described by the dependent claims.

According to a first aspect of the invention there is provided an X-ray tube. The X-ray tube comprises (a) an electron source, which is adapted to generate an electron beam, (b) an anode, which is arranged within the electron beam and which comprises a first focal spot portion and a second focal spot portion, whereby the second focal spot portion is spatially separated from the first focal spot portion, (c) a first electron beam manipulation unit, which is adapted to interact with the electron beam, when the electron beam impinges onto the first focal spot portion, and (d) a second electron beam manipulation unit, which is adapted to interact with the electron beam, when the electron beam impinges onto the second focal spot portion.

This aspect of the invention is based on the idea that the parameters for modulating the electron beam impinging onto the first respectively the second focal spot portion can be optimized individually while taking into account the spatial position on the anode target. In other words, the parameters for optimally manipulating the electron beam can be adjusted for each focal spot portion separately.

In this respect the term "electron beam manipulation" includes a variety of different interactions between the electron beam and the first respectively the second electron beam manipulation unit. For instance, the electron beam manipulation units may change the exact position of the focal spot being generated by the electrons impinging onto the anode. Thereby, the electron beam manipulation units are adapted to at least slightly deflect the electron beam. Further, the electron beam manipulation units may also be adapted to change the intensity of the electron beam for instance by applying appropriate (high) voltage levels to an electrode of the corresponding electron beam manipulation unit. Thereby, the intensity of the generated X-ray beam will be manipulated accordingly. By temporally varying the electron beam intensity between a maximal value and zero, the generated X-ray beam can be switched on and off in a controlled manner. This means that the beam manipulation units may act as grid switches, which are widely known in the field of electron optics.

According to an embodiment of the invention (a) the anode is rotatable around a z-axis and (b) the second focal spot portion is spatially separated from the first focal spot portion along a z-direction being oriented parallel to the z-axis. This may provide the advantage that the concentration of the heat load of the anode may be reduced significantly because even when the electron beam generates only two discrete focal spots the heat load generated by a high-energy electron beam is distributed over a comparatively wide region on the anode surface.

According to a further embodiment of the invention the (a) the first electron beam manipulation unit is a first electron beam focusing and/or deflection unit and/or (b) the second electron beam manipulation unit is a second electron beam focusing and/or deflection unit. This provides the advantage that the X-ray tube may allow for an individual electron beam focusing of both a first focal spot being generated at the first focal spot portion and a second focal spot being generated at the second focal spot portion, respectively. Thereby, the first electron beam focusing can be located in close proximity to the first focal spot portion and/or the second electron beam focusing can be located in close proximity to the second focal spot portion, respectively. Therefore, the electron beam focusing can be accomplished close to the corresponding focal spot such that an inherent self-defocusing of the electron beam can be neglected in good proximity, because the electron beam path between the electron beam focusing unit and the corresponding focal spot is comparatively short.

The first respectively the second electron beam focusing units may allow for an electric and/or a magnetic focusing. Thereby, electric and/or magnetic multipole arrangements may be employed. For a magnetic focusing preferably magnetic quadrupoles or even higher multipoles can be used. For an electric focusing electric lenses can be used, which may comprise hollow cylinders on different potentials with respect to ambient or with respect to the anode surface.

In particular when a magnetic focusing is used, the above-described individual electron beam manipulation respectively focusing may allow for a faster switching over between the first and the second focal spot. This is based on the fact that compared to using a single electron beam focusing unit only, the focusing parameters of the individual electron beam focusing units do typically not have to be changed such excessively. Therefore, the time being needed for optimally adjusting the focusing parameters is no more much longer than the desired transition time between the two focal spots. This may be in particular advantageous for computed tomography with large area detectors and multiple focal spots in the employed X-ray tube. Thereby, every focal spot is used only for a certain period of the whole rotation cycle duration of the CT gantry, which supports both the X-ray tube and the X-ray detector rotating around the object under examination. The mentioned certain period, which corresponds to one projection view, typically lasts about 100 µs to 1 ms.

The described individual electron beam focusing has the further advantage that the focal spots being generated at different z-positions may be focused in a different manner such that a re-focusing is possible in order to compensate for different anode angles i.e. the angle between the target surface, from which the X-ray beam emerges and the z-direction. In this respect it has to be mentioned that for full coverage of the detector in z-direction, the anode angle will need to depend on the z-position of the focal spot. Of course this matter of fact also holds for tubes with multiple focal spots separated in z-direction.

Further, the spatial resolution of the CT-system is determined by the apparent optical focal spot size as it is seen by the object i.e. projected into a plane perpendicular to the line connecting the focal spot and an given voxel located within the object. Thereby, the larger the anode angle is, the shorter the physical focal spot should be. Therefore, in order to keep the optical X-ray focal spot constant and simultaneously allow for different anode angles on the target surface, the physical focal spot, i.e. the area, which is being hit by the e-beam, needs to be adjusted. The first and the second focusing means can take care of such adjustments such that for all focal spots an appropriate focal spot size and focal spot shape can be provided.

In other words, the provision of a dedicated electron beam focusing unit for each focal spot position gives an additional degree of freedom to individually adjust the size and the shape of each focal spot. This allows for an individual beam size adjustment by taking into account the anode angle of the particular focal spot.

According to a further embodiment of the invention (a) the anode comprises a cylindrical anode body, (b) the first focal spot portion is a first protrusion, which is arranged along the circumference of the cylindrical body at least partially, and (c) the second focal spot portion is a second protrusion, which is arranged along the circumference of the cylindrical body at least partially. Thereby, the cylindrical anode body is aligned with the z-axis. This means that the anode is capable of rotating around the symmetric axis of the cylindrical anode body.

The protrusion may extend from the cylindrical anode body in a predominantly radial direction with respect to the z-axis. The protrusions are preferably more or less thick blades, which are made from a material being typically used as an anode material such as tungsten or a composition comprising tungsten and rhenium. In order to withstand a typically very large thermal load produced by the impinging electrons, the blades may comprise two layers, a first layer for converting the decelerated electrons into X-radiation and a second layer providing for a thermal expansion compensation or heat storage.

An upper surface of the blades may be angulated with respect to a plane being oriented perpendicular to the rotational axis. Preferably, the generated first respectively second focal spot has the shape of an elongated rectangle. Since the X-rays generated within the focal spot are emitted in a radial direction outward from the rotational axis, the projection of the focal spot perpendicular to the direction of the emitted X-rays is much smaller thus leading to a comparatively small focal spot size, which in turn increases the sharpness of X-ray projection images. Preferably, in this projection the first respectively the second focal spot has the shape of a square.

According to a further embodiment of the invention the first protrusion comprises at least one first cutout such that (a) in a first angular position of the anode an electron beam propagating predominantly parallel to the z-axis impinges onto the first protrusion and (b) in a second angular position of the anode the electron beam propagating predominantly parallel to the z-axis impinges onto the second protrusion. Such an arrangement of the first and the second protrusion may allow to easily shift the position of the active focal spot along the z-axis in a precise and discrete manner. Thereby, the length of the discrete shift is determined by the spacing between the first and the second protrusion.

The described geometry of the anode represents a simple solution in order to discretely shift the focal spot between two focal spot positions, which are widely separated from each other. Of course, the frequency of the focal spot shifts is synchronized with the phase of rotation of the anode. This means that the rotation of the anode has to be controlled precisely such that when employing the generated X-ray beam it is always clear from which focal spot the actual X-ray beam is originating. However, in the technical field of multiple focus X-ray tubes there are known various ways how to realize a precise rotation control for the anode. Such a control may be either an open loop control or a closed loop control.

By selecting the size of the cutout respectively the angular range of the cutout one can determine the time slice during which the X-ray beam is originating from the second focal spot. Of course, when the first protrusion comprises two or more cutouts, there are two or more time slices within one revolution period of the anode, during which time slices the second focal spot is active. This means that within one anode revolution the origin on the X-ray beam switches back and forth several times between the first focal spot being located at the first protrusion and the second focal spot being located at the second protrusion.

It has to be mentioned that also the second protrusion may comprise a second cutout, which is arranged with an angular offset with respect to the first cutout. This may allow for providing a further respectively a third protrusion at the anode body such that the active focal spot can be discretely shifted between three spatially separated focal spot positions.

According to a further embodiment of the invention (a) the electron beam impinging onto the first focal spot portion traverses a first interaction region of the first beam manipulation unit, and (b) the electron beam impinging onto the second focal spot portion traverses the first interaction region of the first beam manipulation unit and a second interaction region of the second beam manipulation unit. This means that a focusing of the electron beam impinging onto the second focal spot portion may be accomplished by both the first and the second beam manipulation unit. By contrast thereto, a focusing of the electron beam impinging onto the first focal spot portion may be accomplished by the first beam manipulation unit only. In this respect the term interaction region is defined by the spatial region in which a force, in particular an electric and/or a magnetic force, can be exerted on the electrons of the electron beam such that the direction of propagation and/or the intensity distribution of the electron beam is changed.

This embodiment may allow for an in particular easy mechanical and geometric setup of all components being used for the described X-ray tube. In particular it is not necessary to provide for a beam switch element, which is adapted to selectively direct the electron beam either to the first beam manipulation unit or to the second beam manipulation unit.

According to a further embodiment of the invention the X-ray tube further comprises a control unit, which is coupled to the first beam manipulation unit and to the second beam manipulation unit. Thereby, (a) the control unit is adapted to control the first beam manipulation unit in such a manner that the first beam manipulation unit is only active when the electron beam impinges onto the first focal spot portion and (b) the control unit is adapted to control the second beam manipulation unit in such a manner that the second beam manipulation unit is only active when the electron beam impinges onto the second focal spot portion. This may provide the advantage that the parameters for controlling the first respectively the second beam manipulation unit are basically constant or are only slowly varying with time. This makes it more easy to precisely focus the electron beam onto the designated focal spot portion.

According to a further embodiment of the invention the X-ray tube further comprises (a) a third focal spot portion, which is formed at the anode and which is spatially separated from the first focal spot portion and from the second focal spot portion, and (b) a third electron beam manipulation unit, which is adapted to interact with the electron beam, when the electron beam impinges onto the third focal spot portion. This may provide the advantage that the active focal spot can be discretely shifted between three different focal spot positions.

The third focal spot portion and the third electron beam manipulation unit may be realized in accordance with any one of the embodiments described above. In particular the third electron beam manipulation unit may be a third beam focusing unit.

It has to be mentioned that also further focal spot portions and correspondingly further electron beam manipulation units may be provided in order to discretely shift the active focal spot between a variety of different focal spot positions.

According to a further embodiment of the invention the X-ray tube further comprises (a) a further electron source, which is adapted to generate a further electron beam, (b) a further first focal spot portion and a further second focal spot portion, which are formed at the anode, (c) a further first electron beam manipulation unit, which is adapted to interact with the further electron beam, when the further electron beam impinges onto the further first focal spot portion, and (d) a further second electron beam manipulation unit, which is adapted to interact with the further electron beam, when the further electron beam impinges onto the further second focal spot portion. Thereby, the further electron beam and the electron beam impinge onto the anode from different directions.

This may provide the advantage that two independent pairs of focal spot portions can be activated. Thereby, it is possible to generate two different active focal spots, whereby both focal spots may be discretely shifted between respectively two focal spot positions.

This dual electron source embodiment may further provide the advantage that the average length of the electron beam path extending from the electron sources and the corresponding focal spot portion can be reduced compared to a configuration, wherein four focal spot portions are sequentially illuminated by one electron beam being emitted from a single electron source only. This has the effect that it is more easy to adjust the optimal apparent focal spot size on each focal spot portion.

According to a further embodiment of the invention the further electron beam and the electron beam impinge onto the anode from opposite directions. This may provide the advantage that both electron sources can be arranged lateral with respect to the anode such that there are no or at least only minor spatial restrictions for arranging the four different electron beam manipulation units. Thereby, a collision between these components and the various generated X-ray beams can be effectively avoided.

According to a further aspect of the invention there is provided an X-ray system, in particular a medical X-ray imaging system like a computed tomography system. The provided X-ray system comprises at least one X-ray tube according to any one of the above-described embodiments.

This aspect of the invention is based on the idea that the above-described X-ray tube may be used for various X-ray systems in particular for medical diagnosis.

One may take benefit from illuminating an object under examination with two different sets of X-ray beams, whereby the two X-ray sets penetrate the object under at least slightly different illumination angles. When using a detector array for sensing the X-ray beams having traversed the object, one can design the X-ray system such that the so-called interleaving technique is applied. Thereby, neighboring X-rays originating from different focal spots are separated from each other by a distance being half of the distance between neighboring X-rays in the case when only one focal spot is used. This has the advantage that when the two X-ray acquisitions being assigned to the two focal spots are combined in an appropriate manner, the spatial resolution of the X-ray system may be enhanced. Under optimal conditions the spatial resolution may be doubled.

A further advantage of the described method can be exploited in computed tomography (CT) when comparatively large objects are examined. By switching the position of the active focal spot in an axial direction with respect to a rotational axis of a CT scanning unit, additional projection views may be generated for each view angle of the scanning unit, which scanning unit comprises the X-ray tube and a corresponding X-ray detector. This will allow to employ smaller X-ray detectors without having the disadvantage that for a certain view angle border regions of the object under examination are not located within a cone-shaped or fan-shaped X-ray beam originating from a single focus X-ray tube and impinging onto the X-ray detector.

It has to be mentioned that the described X-ray system may also be used for other purposes than medical imaging. For instance the described X-ray system may also be employed e.g. for security systems such as baggage inspection apparatuses.

According to a further aspect of the invention there is provided a method for generating X-rays, in particular for generating X-rays being used for medical X-ray imaging like computed tomography. The provided method comprises using an X-ray tube according to any one of the above-described embodiments of the X-ray tube.

It has to be noted that embodiments of the invention have been described with reference to different subject matters. In particular, some embodiments have been described with reference to apparatus type claims whereas other embodiments have been described with reference to method type claims. However, a person skilled in the art will gather from the above and the following description that, unless other notified, in addition to any combination of features belonging to one type of subject matter also any combination between features relating to different subject matters, in particular between features of the apparatus type claims and features of the method type claims is considered to be disclosed with this application.

The aspects defined above and further aspects of the present invention are apparent from the examples of embodiment to be described hereinafter and are explained with reference to the examples of embodiment. The invention will be described in more detail hereinafter with reference to examples of embodiment but to which the invention is not limited.

DETAILED DESCRIPTION

Figure 1:
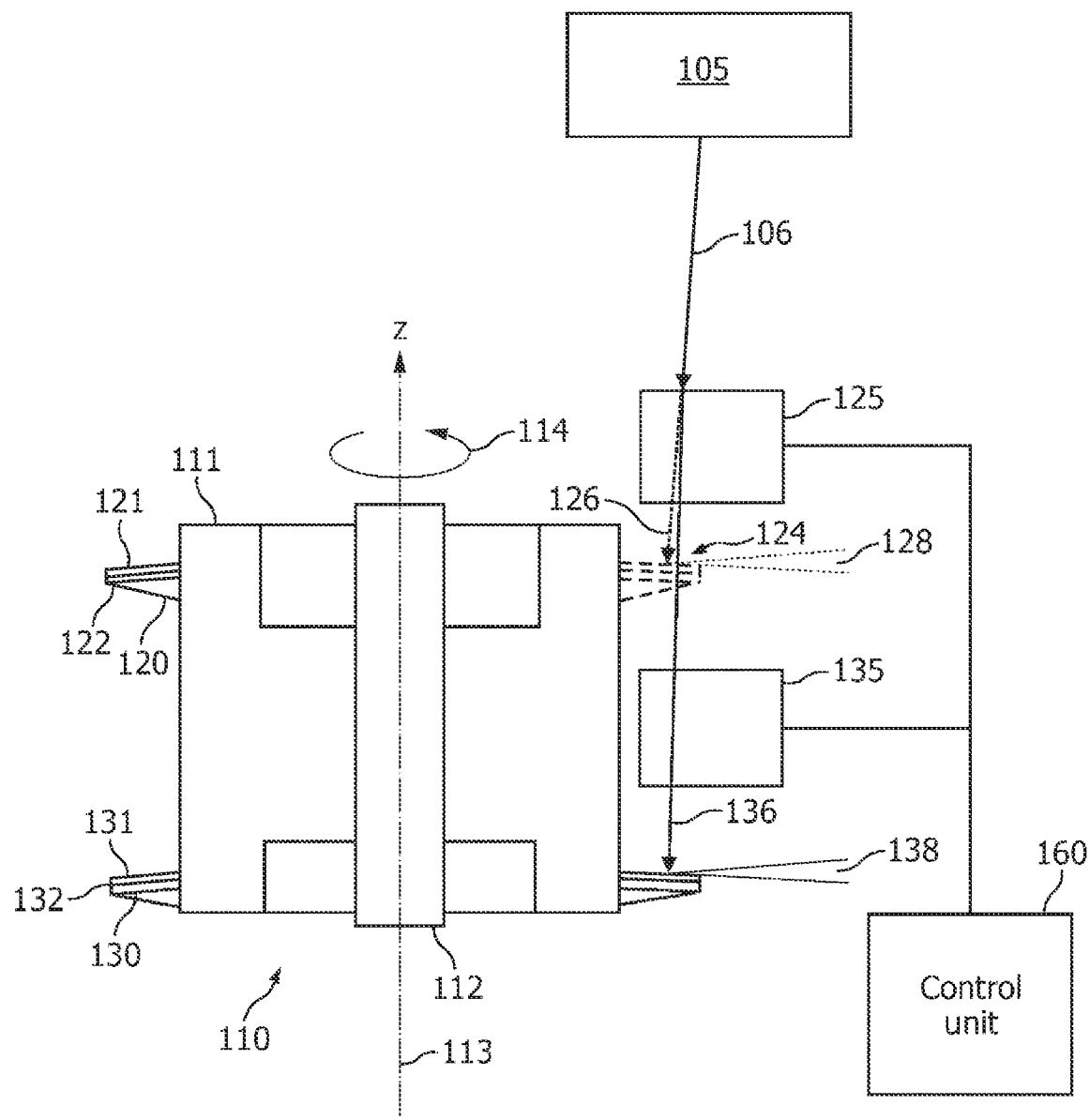
FIG. 1 shows a cross sectional view of a dual focus X-ray tube comprising two focal sport portions being respectively arranged along the circumference of a cylindrical anode body.

The illustration in the drawing is schematically. It is noted that in different figures, similar or identical elements are provided with the same reference signs or with reference signs, which are different from the corresponding reference signs only within the first digit.

FIG. 1 shows a cross sectional view of a dual focus X-ray tube 100. The X-ray tube comprises an electron source 105, which is adapted to generate an electron beam 106 projecting along a propagation axis. According to the embodiment described here, the electron source 105 comprises a hot cathode or a field emission cathode.

The X-ray tube 100 further comprises an anode 110, which is arranged within the electron beam 106. The anode 106 comprises a substantially cylindrical anode body 111, which is supported within a not depicted bearing by means of an anode axis 112. The bearing allows for a rotational movement 114 of the anode 110 around a rotational axis 113 being aligned with a z-axis.

The anode 110 comprises a first focal spot portion 120, which is formed as a first protrusion 120 being arranged partially along the circumference of the cylindrical anode body 111. The first protrusion 120 comprises a target layer 121, which is made from a tungsten/rhenium composition and which has a thickness of approximately 1 mm. The first protrusion 120 further comprises thermal compensation layer 122, which is arranged directly underneath the target layer 121.

The anode 110 further comprises a second focal spot portion 130, which is formed as a second protrusion 130 being arranged along the circumference of the cylindrical anode body 111. The second protrusion 130 corresponds to the first protrusion 120. Therefore, also the second protrusion 130 comprises a target layer 131 and a thermal compensation layer 132.

The first protrusion 120 comprises a plurality of cutouts 124, wherein in the depicted cross sectional view only one cutout 124 can be seen. The cutouts 124 are distributed along the circumference of the cylindrical anode body 111. Therefore, depending on the angular position of the anode 110 the electron beam 106 impinges along a first electron beam path 126 onto the target layer 121 of the first protrusion 120 or along a second electron beam path 136 onto the target layer 131 of the second protrusion 130. In case the electron beam 106 impinges onto the first protrusion 120 a first X-ray beam 128 will be generated. In case the electron beam 106 impinges onto the second protrusion 130 a second X-ray beam 138 will be generated. In the angular state depicted in FIG. 1 the second X-ray beam 138 is generated respectively active. Therefore, the first X-ray beam 128 is indicated with dashed lines only.

In order to allow for an individual focusing of the electron beam 106 onto the first protrusion 120 respectively the second protrusion 130, there are provided two electron beam manipulation units, a first electron beam manipulation unit 125 and a second electron beam manipulation unit 135. According to the embodiment described here, the electron beam manipulation units 125, 135 are used for focusing the electron beam 106 such that on both protrusions 120 and 130 focal spots with an appropriate spot size will be generated.

The two electron beam manipulation units 125, 135 are coupled to a control unit 160, which is adapted to control the first beam manipulation unit 125 in such a manner that the first beam manipulation unit 125 is only active when the electron beam 106 impinges onto the first focal spot portion 120. Further, the control unit 160 is adapted to control the second beam manipulation unit 135 in such a manner that the second beam manipulation unit 135 is only active when the electron beam 106 impinges onto the second focal spot portion 135. This provides the advantage that the parameters for controlling the two beam manipulation units 125, 135 are basically constant or are only slowly varying with time. This makes it more easy to precisely focus the electron beam onto the designated focal spot portion even if the toggling frequency between the two focal spots is comparatively large.

As one can further seen from FIG. 1, the first beam manipulation unit 125 is arranged both in the first electron beam path 126 and the second electron beam path 138. Therefore, the first beam manipulation unit 125 can be used to interact with the electron beam 106 independent from the destination of the electron beam 106. By contrast thereto, the second beam manipulation unit 135 can be used only to deflect respectively focus the second electron beam 106 after it has been modified by means of the first beam manipulation unit 125. However, as has been described above the two beam manipulation units 125, 135 are controlled in such a manner, that they provide in an alternating manner a focusing of the electron beam propagating along the first electron beam path 126 respectively the second electron beam path 136. This means that the first beam manipulation unit 125 is repeatedly switched off when the second beam manipulation unit 135 is switched on. The same holds mutatis mutandis i.e. the second beam manipulation unit 135 is repeatedly switched off when the first beam manipulation unit 125 is switched on.

Alternatively, the second beam manipulation unit 135 can be understood as a compensation for optimally focusing the electron beam propagating along the second beam path 136 such that an appropriate focus size will be generated on the second protrusion 130. In this context the first beam manipulation unit 125, which is always activated independent from the actual angular position of the anode 110, is optimized for focusing the electron beam propagating along the first beam path 126. The second beam manipulation unit 135 is used for focusing the electron beam 106 propagating along the second X-ray beam path 136, whereby the previous focusing by means of the first beam manipulation unit 125 is taken into account. This means that also the second beam manipulation unit 135 can be permanently switched on.

According to the embodiment described here the anode 110 including the first respectively the second protrusion may have a diameter within the range from approximately 15 cm to approximately 40 cm. The height of the anode body is approximately 15 cm. The distance between the first and the second protrusion along the z-axis is approximately 10 to 14 cm. However, it has to be pointed out that of course also other dimensions might be applicable for realizing the invention.

Figure 2A:
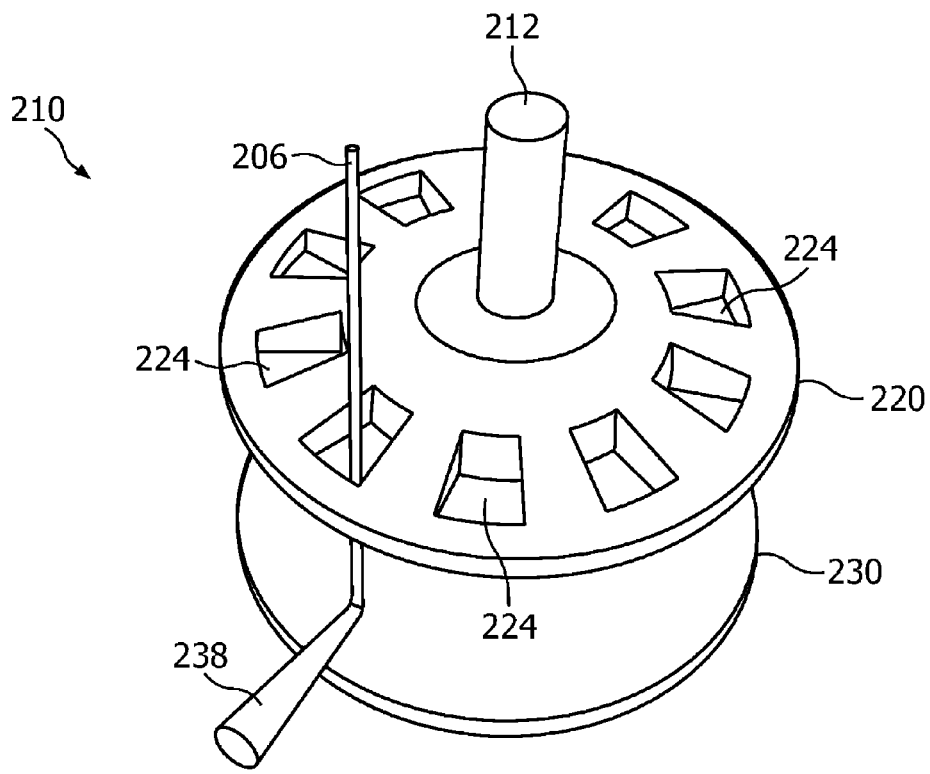
FIGS. 2a and 2b show two perspective views illustrating an anode at two different rotational states.
Figure 2B:
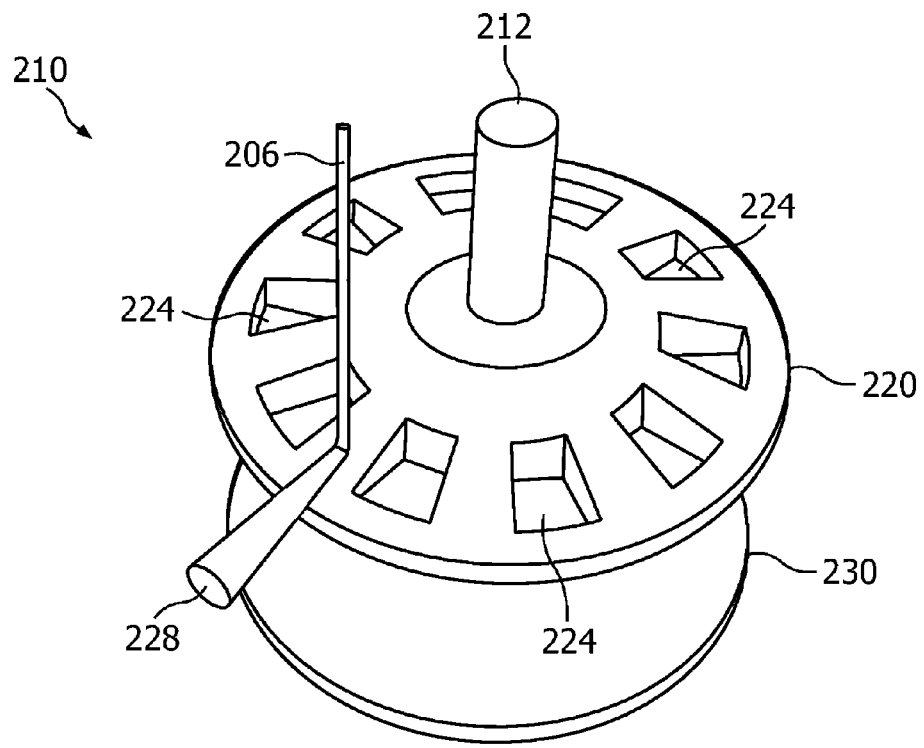

FIGS. 2a and 2b show two perspective views illustrating an anode 210 at two different rotational states. The anode 210 comprises two focal sport portions, a first focal sport portion 220 and a second focal sport portion 230. The anode 210 further comprises an anode axis 212, which can be accommodated in a not depicted bearing allowing for a rotational movement of the anode 210. The first focal spot portion 220 comprises a plurality of cutouts 224 for letting an electron beam 206 pass towards the second focal spot portion 230, when the anode 210 is in an angular position such that the electron beam does not impinge onto the first focal sport portion 220.

FIG. 2a shows the anode 210 in a rotational state, wherein the electron beam passes through a cutout 224. Correspondingly, a second X-ray beam 238 originating from the second protrusion 230 will be generated. FIG. 2b shows the anode 210 in a rotational state, wherein the electron beam impinges onto a protrusion portion located in between two neighboring cutouts 224. Correspondingly, a first X-ray beam 228 originating from the first protrusion 220 will be generated.

Figure 3:
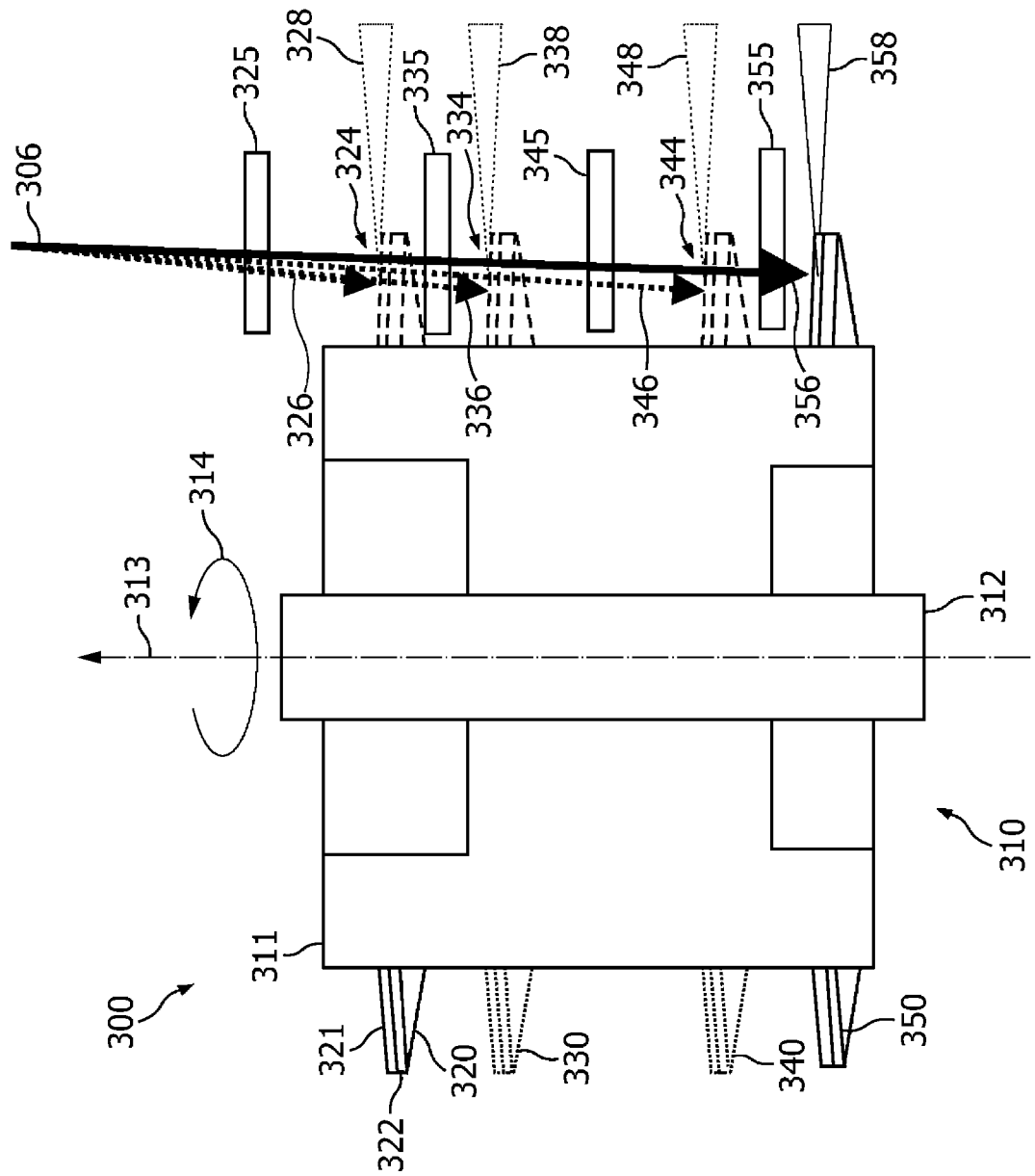
FIG. 3 shows a cross sectional view of a multiple focus X-ray tube comprising four focal sport portions being arranged along the circumference of a cylindrical anode body.

FIG. 3 shows a cross sectional view of a multiple focus X-ray tube 300. In accordance with the X-ray tube 100 shown in FIG. 1, the X-ray tube 300 comprises an anode 310, which itself comprises a cylindrical anode body 311 and an anode axis 312 such that the anode 310 is rotatable around a rotational axis 313 being aligned with a z-axis. The rotational direction of the anode 310 is indicated by the arrow 314.

By contrast to the anode 110 shown in FIG. 1, the anode 310 is equipped with four focal spot portions, a first focal spot portion 320, a second focal spot portion 330, a third focal spot portion 340 and a fourth focal spot portion 350. Each focal spot portion 320, 330, 340 and 350 comprises a target layer 321 made from a tungsten/rhenium composition and a thermal composition layer 322.

The first focal spot portion 320, the second focal spot portion 330 and the third focal spot portion 340 are equipped with cutouts 324, 334 and 344, respectively. The cutouts 324, 334 and 344 are arranged with respect to each other in such manner, that when rotating the anode 310 an electron beam 306 being directed to the anode 310 will sequentially impinge (a) on the first focal spot portion 320, (b) on the second focal spot portion 330, (c) on the third focal spot portion 340 and (d) on the fourth focal spot portion. Thereby, the electron beam 306 will sequentially propagate along (a) a first electron beam path 326 terminating at the first protrusion 320, (b) a second electron beam path 336 terminating at the second protrusion 330, (c) a third electron beam path 346 terminating at the third protrusion 340 and (d) a fourth electron beam path 356 terminating at the fourth protrusion 350. As a consequence, there will be generated in a sequential manner (a) a first X-ray beam 328, (b) a second X-ray beam 338, (c) a third X-ray beam 348 and (d) a fourth X-ray beam 358.

FIG. 3 depicts the anode 310 in a rotational position wherein the fourth X-ray beam 358 is switched on. Correspondingly, the first X-ray beam 328, the second X-ray beam 338 and the third X-ray beam 348 are switched off. Therefore, these X-ray beams 328, 338, 348 are indicated with dashed lines.

In order to allow for a precise focusing of the electron beam 306 onto all protrusions 320, 330, 340 and 350, the X-ray tube comprises four electron beam manipulation units, a first electron beam manipulation unit 325, a second electron beam manipulation unit 335, a third electron beam manipulation unit 345 and a fourth electron beam manipulation unit 355. Thereby, the first electron beam manipulation unit 325 is assigned to the first protrusion 320, the second electron beam manipulation unit 335 is assigned to the second protrusion 330, the third electron beam manipulation unit 345 is assigned to the third protrusion 340 and the fourth electron beam manipulation unit 355 is assigned to the fourth protrusion 350. An in particular precise and reliable focusing of the electron beam 306 can be achieved, if the respective electron beam manipulation unit is arranged in close proximity to the corresponding protrusion.

Figure 4:
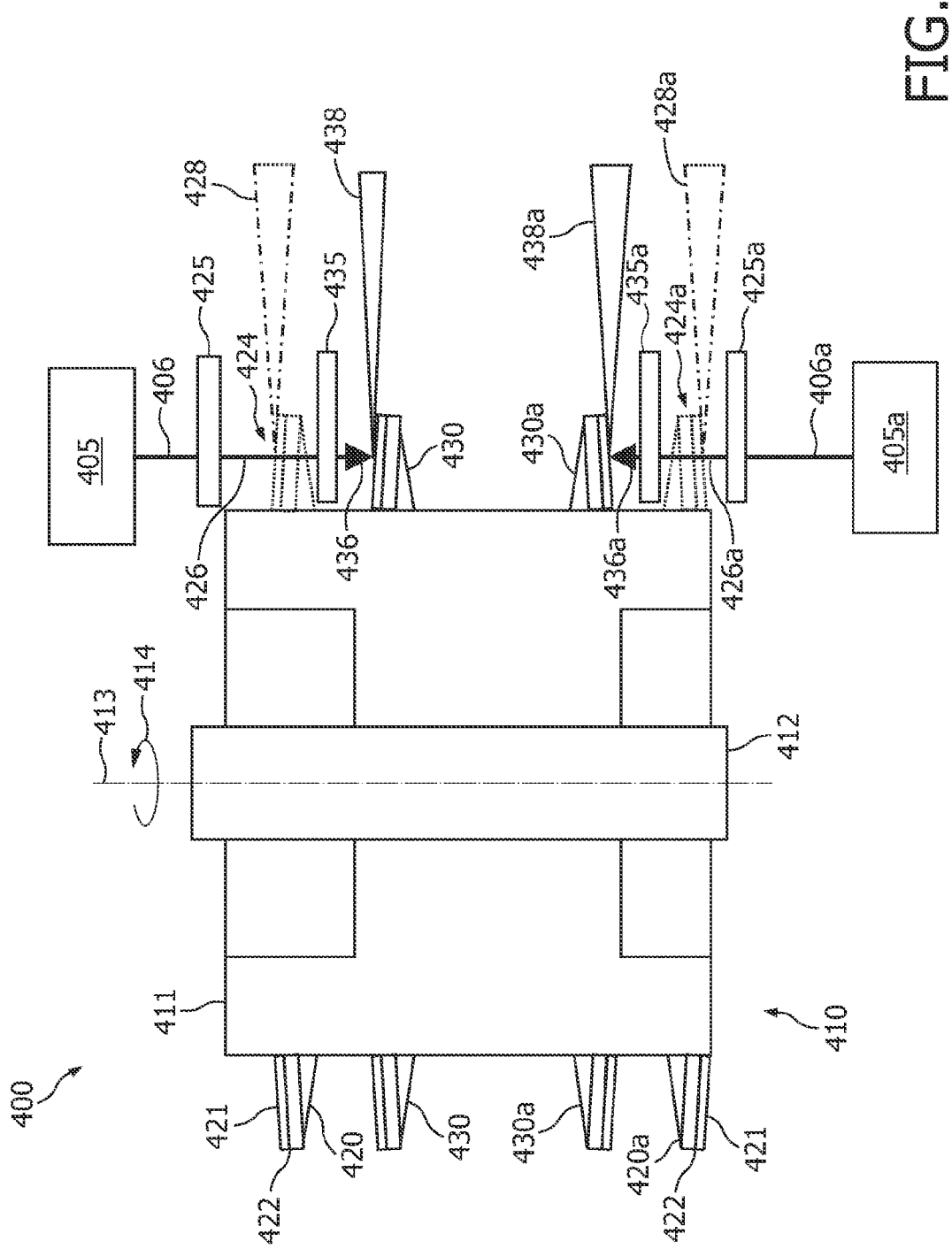
FIG. 4 shows a cross sectional view of a multiple focus X-ray tube comprising two electron sources and four focal sport portions, wherein respectively two focal sport portions are assigned to respectively one of the electron sources.

FIG. 4 shows a cross sectional view of a multiple focus X-ray tube 400 according to another embodiment in accordance with the present invention. The X-ray tube 400 comprises two electron sources, a first electron source 405 generating an electron beam 406 and a further electron source 405a generating a further electron beam 406a. The two electron beams 406 and 406a are directed to an anode 410. As can be seen from FIG. 4, the further electron beam 406a is directed to the anode 410 in a substantially opposite direction with respect to the electron beam 406.

In accordance with the embodiments described with reference to FIGS. 1 and 3, also the anode 410 comprises an anode body 411 and an anode axis 412. The anode 410 is rotatable around a rotational axis 413 being oriented parallel with a z-axis. The rotary movement is indicated with an arrow 414.

In accordance with the anode 310 shown in FIG. 3, also the anode 410 is equipped with four focal spot portions. However, two of these focal sport portions, a first focal spot portion 420 and a second focal spot portion 430, are assigned to the electron source 405. The other two of these focal sport portions, a further first focal spot portion 420a and a further second focal spot portion 430a, are assigned to the further electron source 405a.

Each focal spot portion 420, 430, 420a and 420b comprises a target layer 421 made from a tungsten/rhenium composition and a thermal composition layer 422. As can be seen from FIG. 4, the focal spot portions 420a and 430b are oriented upside down with respect to the focal spot portions 420 and 430. This orientation makes sure that both the electron beam 406 and the further electron beam 406a impinges onto a target layer 421 and not onto a thermal compensation layer 422.

The first focal spot portion 420 comprises a plurality of cutouts 424 such that when rotating the anode 410 the electron beam 406 impinges onto the first focal spot portion 420 and onto the second focal spot portion 430 in a sequential manner. Thereby, the electron beam 406 will sequentially propagate along a first electron beam path 426 terminating at the first protrusion 420 and a second electron beam path 436 terminating at the second protrusion 430. As a consequence, there will be generated in a sequential manner a first X-ray beam 428 and a second X-ray beam 438.

The same holds for the further first focal spot portion 420a, which also comprises a plurality of further cutouts 424a such that the further electron beam 406a impinges onto the further first focal spot portion 420a and onto the further second focal spot portion 430a in a sequential manner. Thereby, the further electron beam 406a will sequentially propagate along a further first electron beam path 426a terminating at the further first protrusion 420a and a further second electron beam path 436a terminating at the further second protrusion 430a. As a consequence, there will be generated in a sequential manner a further first X-ray beam 428a and a further second X-ray beam 438a.

In other words, the X-ray tube 400 allows for a simultaneous generation of two X-ray beams. Thereby, the focal spot position of a first one of these X-ray beams can be shifted in a periodic manner in between the first protrusion 420 and the second protrusion 430. The focal spot position of the second one of these X-ray beams can be shifted in a periodic manner in between the further first protrusion 420a and the further second protrusion 430a.

FIG. 4 depicts the anode 410 is a rotational position wherein the second X-ray beam 438 and the further second X-ray beam 438a are switched on. Correspondingly, the first X-ray beam 428 and the further first X-ray beam 438 are switched off. Therefore, the first X-ray beam 428 and the further first X-ray beam 438 are indicated with dashed lines.

It has to be mentioned that also the electron source 405 and the further electron source 405 can be operated in an alternating manner e.g. by employing known grid switches. Thereby, it can be realized that at any time there is only one of the X-ray beams 428, 438, 428a and 438a switched on whereas the other X-ray beams are switched off.

In order to allow for a precise focusing of the electron beam 406 respectively the electron beam 406a onto the protrusions 420 and 430 respectively the protrusions 420a and 430a, the X-ray tube 400 comprises four beam manipulation units, a first beam manipulation unit 425, a second beam manipulation unit 435, a further first beam manipulation unit 425a and a further second beam manipulation unit 425a. Thereby, the first beam manipulation unit 425 is assigned to the first protrusion 420, the second beam manipulation unit 435 is assigned to the second protrusion 430, the further first beam manipulation unit 425a is assigned to the further first protrusion 420a and the further second beam manipulation unit 435a is assigned to the further second protrusion 430a. An in particular precise and reliable focusing of the electron beam 406 respectively the further electron beam 406a can be achieved, if the respective beam manipulation unit is arranged in close proximity to the corresponding protrusion.

Figure 5:
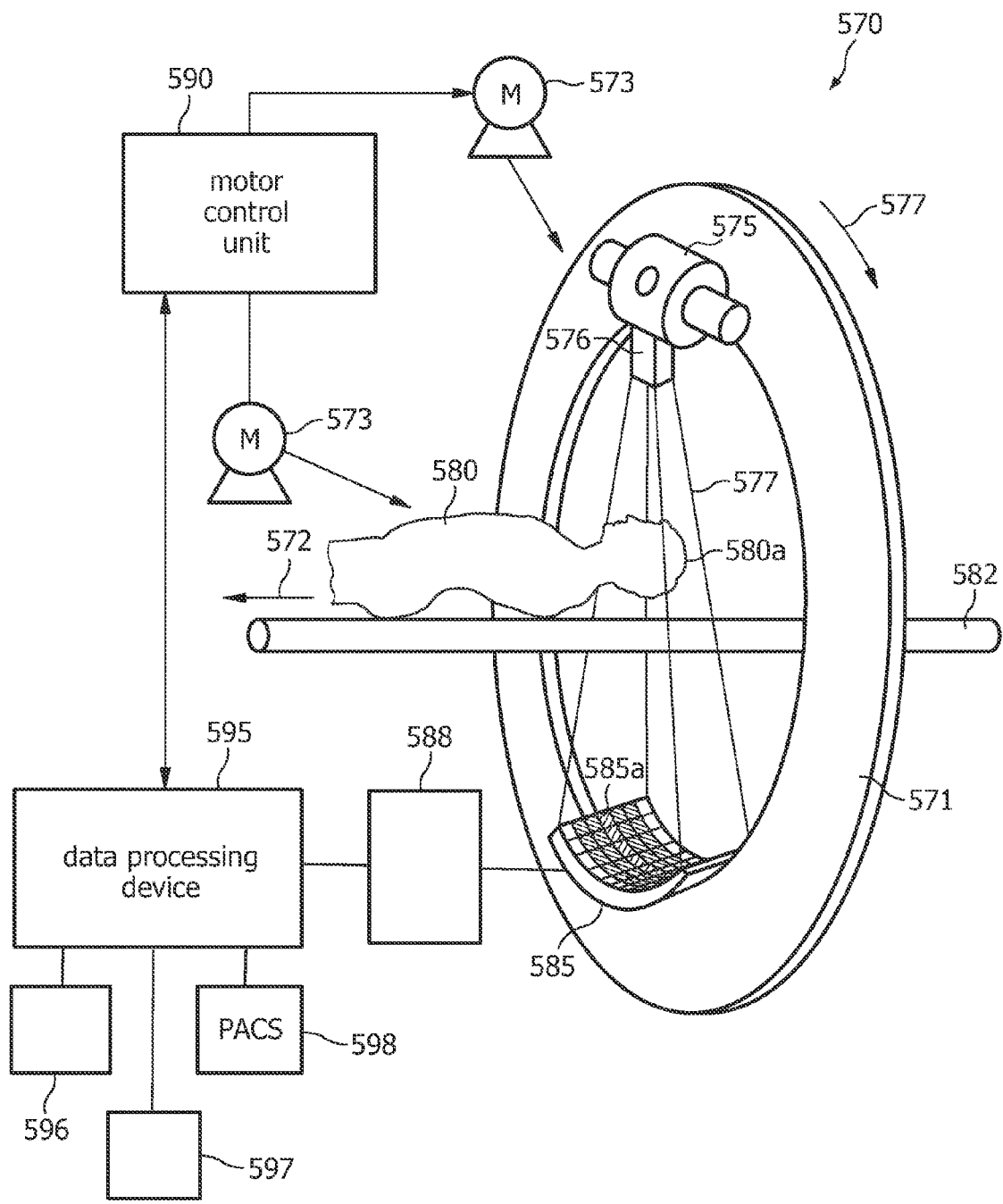
FIG. 5 shows a simplified schematic representation of a computed tomography (CT) system according to an embodiment of the present invention, wherein the CT system is equipped with a single multiple focus X-ray tube.

FIG. 5 shows a computer tomography apparatus 570, which is also called a CT scanner. The CT scanner 570 comprises a gantry 571, which is rotatable around a rotational axis 572. The gantry 571 is driven by means of a motor 573.

Reference numeral 575 designates a source of radiation such as an X-ray tube, which emits polychromatic radiation 577. The CT scanner 570 further comprises an aperture system 576, which forms the X-radiation being emitted from the X-ray tube 575 into a radiation beam 577.

The radiation beam 577, which may by a cone-shaped or a fan-shaped beam 577, is directed such that it penetrates a region of interest 580a. According to the embodiment described herewith, the region of interest is a head 580a of a patient 580.

The patient 580 is positioned on a table 582. The patient's head 580a is arranged in a central region of the gantry 571, which central region represents the examination region of the CT scanner 570. After penetrating the region of interest 580a the radiation beam 577 impinges onto a radiation detector 585. In order to be able to suppress X-radiation being scattered by the patient's head 580*a* and impinging onto the X-ray detector 585 under an oblique angle there is provided a not depicted anti scatter grid. The anti scatter grid is preferably positioned directly in front of the detector 585.

The X-ray detector 585 is arranged on the gantry 571 opposite to the X-ray tube 575. The detector 585 comprises a plurality of detector elements 585*a* wherein each detector element 585*a* is capable of detecting X-ray photons, which have been passed through the head 580*a* of the patient 580.

During scanning the region of interest 580*a*, the X-ray source 585, the aperture system 576 and the detector 585 are rotated together with the gantry 571 in a rotation direction indicated by an arrow 587. For rotation of the gantry 571, the motor 573 is connected to a motor control unit 590, which itself is connected to a data processing device 595. The data processing device 595 includes a reconstruction unit, which may be realized by means of hardware and/or by means of software. The reconstruction unit is adapted to reconstruct a 3D image based on a plurality of 2D images obtained under various observation angles.

Furthermore, the data processing device 595 serves also as a control unit, which communicates with the motor control unit 590 in order to coordinate the movement of the gantry 571 with the movement of the table 582. A linear displacement of the table 582 is carried out by a motor 583, which is also connected to the motor control unit 590.

During operation of the CT scanner 570 the gantry 571 rotates and in the same time the table 582 is shifted linearly parallel to the rotational axis 572 such that a helical scan of the region of interest 580*a* is performed. It should be noted that it is also possible to perform a circular scan, where there is no displacement in a direction parallel to the rotational axis 572, but only the rotation of the gantry 571 around the rotational axis 572. Thereby, slices of the head 580*a* may be measured with high accuracy. A larger three-dimensional representation of the patient's head may be obtained by sequentially moving the table 582 in discrete steps parallel to the rotational axis 572 after at least one half gantry rotation has been performed for each discrete table position.

The detector 585 is coupled to a pre-amplifier 588, which itself is coupled to the data processing device 595. The processing device 595 is capable, based on a plurality of different X-ray projection datasets, which have been acquired at different projection angles, to reconstruct a 3D representation of the patient's head 580*a*.

In order to observe the reconstructed 3D representation of the patient's head 580*a* a display 596 is provided, which is coupled to the data processing device 595. Additionally, arbitrary slices of a perspective view of the 3D representation may also be printed out by a printer 597, which is also coupled to the data processing device 595. Further, the data processing device 595 may also be coupled to a picture archiving and communications system 598 (PACS).

It should be noted that monitor 596, the printer 597 and/or other devices supplied within the CT scanner 570 might be arranged local to the computer tomography apparatus 570. Alternatively, these components may be remote from the CT scanner 570, such as elsewhere within an institution or hospital, or in an entirely different location linked to the CT scanner 570 via one or more configurable networks, such as the Internet, virtual private networks and so forth.

It should be noted that the term "comprising" does not exclude other elements or steps and the "a" or "an" does not exclude a plurality. Also elements described in association with different embodiments may be combined. It should also be noted that reference signs in the claims should not be construed as limiting the scope of the claims.

LIST OF REFERENCE SIGNS

100 X-ray tube
105 electron source
106 electron beam
110 anode
111 anode body
112 anode axis
113 rotational axis/z-axis
114 rotary motion
120 first focal spot portion/first protrusion
121 target layer/tungsten-rhenium layer
122 thermal compensation layer
124 cutout
125 first electron beam manipulation unit
126 first electron beam path
128 first X-ray beam (non active)
130 second focal spot portion/second protrusion
131 target layer/tungsten-rhenium layer
132 thermal compensation layer
135 second electron beam manipulation unit
136 second electron beam path
138 second X-ray beam (active)
160 control unit
206 electron beam
210 anode
212 anode axis
220 first focal spot portion/first protrusion
224 cutout
228 first X-ray beam (active)
230 second focal spot portion/second protrusion
238 second X-ray beam (active)
300 X-ray tube
306 electron beam
310 anode
311 anode body
312 anode axis
313 rotational axis/z-axis
314 rotary motion
320 first focal spot portion/first protrusion
321 target layer/tungsten-rhenium layer
322 thermal compensation layer
324 cutout
325 first electron beam manipulation unit
326 first electron beam path
328 first X-ray beam (non active)
330 second focal spot portion/second protrusion
334 cutout
335 second electron beam manipulation unit
336 second electron beam path
338 second X-ray beam (non active)
340 third focal spot portion/third protrusion
344 cutout
345 third electron beam manipulation unit
346 third electron beam path
348 third X-ray beam (non active)
350 fourth focal spot portion/fourth protrusion
355 fourth electron beam manipulation unit
356 fourth electron beam path
358 fourth X-ray beam (non active)
400 X-ray tube
405 electron source
405*a* further electron source
406 electron beam
406*a* further electron beam
410 anode
411 anode body 412 anode axis
413 rotational axis/z-axis
414 rotary motion
420 first focal spot portion/first protrusion
420a further first focal spot portion/further first protrusion
421 target layer/tungsten-rhenium layer
422 thermal compensation layer
424 cutout
424a further cutout
425 first electron beam manipulation unit
425a further first electron beam manipulation unit
426 first electron beam path
426a further first electron beam path
428 first X-ray beam (non active)
428a further first X-ray beam (non active)
430 second focal spot portion/second protrusion
430a further second focal spot portion/further second protrusion
435 second electron beam manipulation unit
435a further second electron beam manipulation unit
436 second electron beam path
436a further second electron beam path
438 second X-ray beam (active)
438a further second X-ray beam (active)
570 medical X-ray imaging system/computed tomography apparatus
571 gantry
572 rotational axis
573 motor
575 X-ray source/X-ray tube
576 aperture system
577 radiation beam
580 object of interest/patient
580a region of interest/head of patient
582 table
583 motor
585 X-ray detector
585a detector elements
587 rotation direction
588 Pulse discriminator unit
590 motor control unit
595 data processing device (incl. reconstruction unit)
596 monitor
597 printer
598 Picture archiving and communication system (PACS)

The invention claimed is:

1. An X-ray tube comprising
an electron source, which is adapted to generate an electron beam;
an anode, which is arranged within the electron beam and which comprises a first focal spot portion and a second focal spot portion, whereby the second focal spot portion is spatially separated from the first focal spot portion;
a first electron beam manipulation unit, which is adapted to interact with the electron beam, when the electron beam impinges onto the first focal spot portion; and
a second electron beam manipulation unit, which is adapted to interact with the electron beam, when the electron beam impinges onto the second focal spot portion, wherein the first electron beam manipulation unit comprises an individual electron beam manipulation unit (i) assigned and (ii) located in close proximity to the first focal spot portion for separately rendering an electron beam manipulation in close proximity to the first focal spot portion, and wherein the second electron beam manipulation unit comprises an individual electron beam manipulation unit (i) assigned and (ii) located in close proximity to the second focal spot portion for separately rendering an electron beam manipulation in close proximity to the second focal spot portion.

2. The X-ray tube according to claim 1, wherein
the anode is rotatable around a z-axis and wherein
the second focal spot portion is spatially separated from the first focal spot portion along a z-direction being oriented parallel to the z-axis.

3. The X-ray tube according to claim 2, wherein
the first electron beam manipulation unit is a first electron beam focusing and/or deflection unit and/or
the second electron beam manipulation unit is a second electron beam focusing and/or deflection unit.

4. The X-ray tube according to claim 2, wherein
the anode comprises a cylindrical anode body,
the first focal spot portion is a first protrusion, which is arranged along the circumference of the cylindrical body at least partially, and
the second focal spot portion is a second protrusion, which is arranged along the circumference of the cylindrical body at least partially.

5. The X-ray tube according to claim 2, wherein
the first protrusion comprises at least one first cutout such that
in a first angular position of the anode an electron beam propagating predominantly parallel to the z-axis impinges onto the first protrusion, and
in a second angular position of the anode the electron beam propagating predominantly parallel to the z-axis impinges onto the second protrusion.

6. The X-ray tube according to claim 1, wherein
the electron beam impinging onto the first focal spot portion traverses a first interaction region of the first beam manipulation unit, and
the electron beam impinging onto the second focal spot portion traverses the first interaction region of the first beam manipulation unit and a second interaction region of the second beam manipulation unit.

7. The X-ray tube according to claim 6, further comprising:
a control unit, which is coupled to the first beam manipulation unit and to the second beam manipulation unit,
wherein the control unit is adapted to control the first beam manipulation unit in such a manner that the first beam manipulation unit is only active when the electron beam impinges onto the first focal spot portion, and
wherein the control unit is adapted to control the second beam manipulation unit in such a manner that the second beam manipulation unit is only active when the electron beam impinges onto the second focal spot portion.

8. The X-ray tube according to claim 1, further comprising:
a third focal spot portion, which is formed at the anode and which is spatially separated from the first focal spot portion and from the second focal spot portion, and
a third electron beam manipulation unit, which is adapted to interact with the electron beam, when the electron beam impinges onto the third focal spot portion.

9. An X-ray system, in particular a medical X-ray imaging system like a computed tomography system, the X-ray system comprising:
at least one X-ray tube according to claim 1.

10. A method for generating X-rays, in particular for generating X-rays being used for medical X-ray imaging like computed tomography, the method comprising:
using an X-ray tube according to claim 1.

11. An X-ray tube comprising:
an electron source, which is adapted to generate an electron beam;
an anode, which is arranged within the electron beam and which comprises a first focal spot portion and a second focal spot portion, whereby the second focal spot portion is spatially separated from the first focal spot portion;
a first electron beam manipulation unit, which is adapted to interact with the electron beam, when the electron beam impinges onto the first focal spot portion, and
a second electron beam manipulation unit, which is adapted to interact with the electron beam, when the electron beam impinges onto the second focal spot portion, further comprising
a further electron source, which is adapted to generate a further electron beam,
a further first focal spot portion and a further second focal spot portion, which are formed at the anode,
a further first electron beam manipulation unit, which is adapted to interact with the further electron beam, when the further electron beam impinges onto the further first focal spot portion, and
a further second electron beam manipulation unit, which is adapted to interact with the further electron beam, when the further electron beam impinges onto the further second focal spot portion, whereby the further electron beam and the electron beam impinge onto the anode from different directions.

12. The X-ray tube according to claim 11, wherein the further electron beam and the electron beam impinge onto the anode from opposite directions.

13. A method for generating X-rays, in particular for generating X-rays being used for medical X-ray imaging like computed tomography, the method comprising:
using an X-ray tube according to claim 11.

14. The X-ray tube according to claim 13, wherein the first electron beam manipulation unit is a first electron beam focusing and/or deflection unit and/or
the second electron beam manipulation unit is a second electron beam focusing and/or deflection unit.

15. The X-ray tube according to claim 13, wherein
the anode comprises a cylindrical anode body,
the first focal spot portion is a first protrusion, which is arranged along the circumference of the cylindrical body at least partially, and
the second focal spot portion is a second protrusion, which is arranged along the circumference of the cylindrical body at least partially.

16. The X-ray tube according to claim 13, wherein
the first protrusion comprises at least one first cutout such that
in a first angular position of the anode an electron beam propagating predominantly parallel to the z-axis impinges onto the first protrusion, and
in a second angular position of the anode the electron beam propagating predominantly parallel to the z-axis impinges onto the second protrusion.

17. The X-ray tube according to claim 11, wherein
the anode is rotatable around a z-axis and wherein
the second focal spot portion is spatially separated from the first focal spot portion along a z-direction being oriented parallel to the z-axis.

18. The X-ray tube according to claim 11, wherein
the electron beam impinging onto the first focal spot portion traverses a first interaction region of the first beam manipulation unit, and
the electron beam impinging onto the second focal spot portion traverses the first interaction region of the first beam manipulation unit and a second interaction region of the second beam manipulation unit.

19. The X-ray tube according to claim 18, further comprising:
a control unit, which is coupled to the first beam manipulation unit and to the second beam manipulation unit,
wherein the control unit is adapted to control the first beam manipulation unit in such a manner that the first beam manipulation unit is only active when the electron beam impinges onto the first focal spot portion, and
wherein the control unit is adapted to control the second beam manipulation unit in such a manner that the second beam manipulation unit is only active when the electron beam impinges onto the second focal spot portion.

20. The X-ray tube according to claim 11, further comprising:
a third focal spot portion, which is formed at the anode and which is spatially separated from the first focal spot portion and from the second focal spot portion, and
a third electron beam manipulation unit, which is adapted to interact with the electron beam, when the electron beam impinges onto the third focal spot portion.

* * * * *